United States Patent [19]
Weber et al.

[11] Patent Number: 5,165,539
[45] Date of Patent: Nov. 24, 1992

[54] SURGICAL INSTRUMENT TRANSPORT TRAY

[75] Inventors: James M. Weber, Alpharetta, Ga.; Holly J. Reisdorf, Auburn, Mass.

[73] Assignee: Kimberly-Clark Corporation, Neenah, Wis.

[21] Appl. No.: 811,155

[22] Filed: Dec. 19, 1991

[51] Int. Cl.⁵ ............................................. B65D 81/18
[52] U.S. Cl. .................... 206/363; 206/370; 206/439; 206/570; 422/300
[58] Field of Search .......... 206/363, 365–370, 206/438, 439, 570; 422/300, 302, 310

[56] References Cited

U.S. PATENT DOCUMENTS

| | | | |
|---|---|---|---|
| 3,697,223 | 10/1972 | Kovalcik et al. | 21/83 |
| 4,541,992 | 9/1985 | Jerge et al. | 422/310 |
| 4,584,182 | 4/1986 | Sanderson et al. | 422/310 |
| 4,617,178 | 10/1986 | Nichols | 422/310 |
| 4,643,303 | 2/1987 | Arp et al. | 206/370 |
| 4,671,943 | 6/1987 | Wahlquist | 422/300 |
| 4,697,703 | 10/1987 | Will | 206/438 |
| 4,704,254 | 11/1987 | Nichols | 422/28 |
| 4,728,504 | 3/1988 | Nichols | 422/310 |
| 4,750,619 | 6/1988 | Cohen et al. | 206/438 |
| 4,798,292 | 1/1989 | Hauze | 206/439 |
| 4,818,502 | 4/1989 | Taschner | 422/310 |
| 4,854,475 | 8/1989 | Riihimaki et al. | 206/369 |
| 4,889,231 | 12/1989 | Foote et al. | 206/363 |
| 4,915,918 | 4/1990 | Nichols | 422/292 |
| 4,919,888 | 4/1990 | Spence | 422/300 |
| 4,936,152 | 6/1990 | Aldred | 73/863 |
| 5,011,718 | 4/1991 | Patterson | 206/363 |

OTHER PUBLICATIONS

Healthmark Industries Company leaflet Figure identified as "tray".

Primary Examiner—Jimmy G. Foster
Attorney, Agent, or Firm—Patrick C. Wilson

[57] ABSTRACT

Disclosed herein is a surgical instrument transport tray for handling, moving, sterilizing and storing wrapped instrument sterilization pans. With the tray there is less risk of the wrapping being torn or otherwise breached after sterilization of the contents. Without the tray, the wrapping used to maintain the sterility of the contents is sometimes damaged, thereby necessitating the removal of the damaged wrap followed by rewrapping and resterilizing the pan and its contents. The risk of such damage, increased cost and lost time are reduced by way of the present invention.

2 Claims, 2 Drawing Sheets

SURGICAL INSTRUMENT TRANSPORT TRAY

BACKGROUND OF THE INVENTION

The present invention is directed to a surgical instrument transport tray. More specifically, the tray is designed to house, transport and store surgical instrument trays or pans which have been wrapped in a sterilization filter medium such as a sterilization wrap and sterilized.

While a number of the hospital and operating room supplies today are disposable, most hospitals still reuse many if not most of the surgical instruments within the operating room. As a result, each time they are used, they must be washed and resterilized before they can be used again. The sterilization process typically involves the placement of the surgical instruments within a sterilization unit such as an open-top stainless steel pan which has a perforated bottom. The instrument pan is then wrapped in a material which will allow the entry of the sterilant such as steam or ethylene oxide while prohibiting the entry of bacteria or other contaminants after the sterilization process has been completed. Once the instruments have been sterilized, they are kept within the instrument pan in the wrapped configuration until their actual use during a surgical procedure.

To reduce the risk of contamination/infection of the patient and the operating room staff, certain procedures are followed with respect to sterilized instruments. If the barrier provided by the wrapping of the instrument pan is breached at any time prior to the use of the instruments, then the contents are considered contaminated and unusable until the instrument pan has been re-wrapped and resterilized. If the breach in the wrapping is found while setting up the operating room suite the whole suite is considered contaminated and must also be reworked.

The highest probability for breaching these wrapped and sterilized instrument pans is during the transporting and storage of them. To date, hospitals have been attempting to reduce the cuts, holes and tears in the sterilization wrap by cushioning the bottom of the instrument pans either with a huck towel between the instrument pan and the sterilization wrap or with some form of cushioning on the storage shelves, usually in the form of foam or a used linen. This cushioning reduces the amount of shearing motion that the wrap experiences when a wrapped instrument pan is pulled or dragged across the storage shelf, thus reducing the chance for the occurrence of cuts, holes, and tears in the sterilization wrap.

The surgical instrument transport tray of the present invention reduces the number of cuts, holes and tears by protecting the wrap from the shearing motion between the tray and the storage shelf. When the surgical instrument transport tray is used, the bottom of the transport tray accepts the shearing motion of the tray moving across the storage shelf thereby leaving the sterilization wrap undamaged. Additionally, since the material that the tray is made from its tougher than the sterilization wrap, the tray can resist repeated occurrences of the shearing motion between the tray and the shelf.

It is therefore an object of the present invention to provide a surgical instrument transport tray for the sterilization, transportation and storage of surgical instrument pans and other devices requiring sterilization. It is another object of the present invention to provide a surgical instrument transport tray which is compact in nature thereby maximizing the amount of storage space available on storage shelves. These and other objects of the present invention will become more apparent upon a further review of the following specification, drawings and claims.

SUMMARY OF THE INVENTION

The present invention relates to a surgical instrument transport tray for use in conjunction with the handling of instrument sterilization pans or trays. Very typically, hospital operating room instruments are grouped according to procedure and sterilized as a group. Usually this involves placing the preselected instruments within an instrument sterilization pan which is an open-topped stainless steel device commonly known to those skilled in the art. Once the instruments have been placed in the pan, the combination is wrapped and taped. The wrapping material is designed to permit the entrance of sterilants such as steam or ethylene oxide to sterilize the contents while presenting a barrier to the entrance of contaminants such as bacteria once the sterilization process is complete. A critical element to this barrier phenomenon is the fact that the material is not breached in any way such as by being cut, punctured or ripped before being unwrapped immediately preceding a surgical procedure. If the material is breached, then the contents are considered nonsterile and the wrapping and sterilization process must be repeated. This obviously costs time and money.

Unfortunately, the path between the sterilization process and the operating room presents many situations where the wrapping material can be breached. The pans, themselves, are heavy and have sharp edges and corners which can abrade, cut or poke through the sterilization wrap. This is compounded by the fact that the wrapped pans are manually carried on carts to and from the sterilizer units as well as to the storage facilities and the operating rooms.

The transport tray of the present invention provides a physical barrier that surrounds the base and partial sides of the wrapped pan. The support tray itself has a ventilated bottom so that the wrapped pan can be placed inside the support tray and the whole assembly can be sterilized together. The sides of the tray are provided with an extended lip to prevent the contact of the contents of adjoining trays. To facilitate handling and transporting of the tray and its contents, a handle rim depends from the lip in spaced-apart relationship with the sidewalls of the tray so that the tray can be carried while conserving space. Further protection is provided to the nested and wrapped instrument sterilization pan by the use of support members within the tray which lift the wrapped pan up off the top surface of the base member of the tray. In this way the underside of the wrapped pan is less likely to be torn while providing added ventilation. Furthermore, the transport trays when not in use can be stacked to minimize storage space.

DETAILED DESCRIPTION OF THE INVENTION

Figure 4:
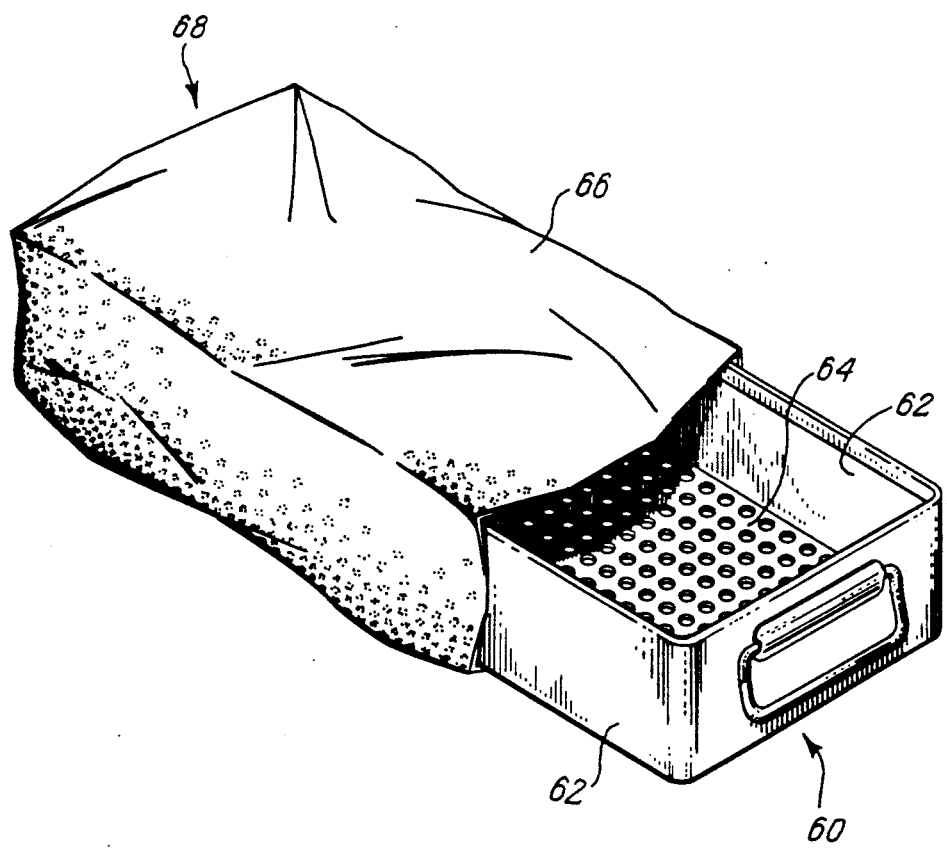
FIG. 4 is a cut-away perspective view of a surgical instrument pan wrapped in a sterilization filter medium and designed to nest within the surgical instrument transport tray shown in FIGS. 1 through 3.

The present invention is directed to a surgical transport tray for moving, storing and protecting wrapped sterilized instrument pans. A typical instrument pan made from stainless steel is shown in FIG. 4. The pan 60 usually has solid sides 62 and a mesh bottom 64 to allow the ingress and egress of sterilization materials such as steam and ethylene oxide. In use, instruments (not shown) needing to be sterilized are placed inside the pan 60 and the combination is wrapped by a sterilization filter medium 66 such as KIMGUARD ® Sterile Wrap and SPUNGUARD ® Sterilization Wrap materials from the Kimberly-Clark Corporation of Neenah, Wis. The loose flaps of the filter medium 66 are taped and the individually wrapped pans 68 are manually placed in sterilization units (not shown). Once the sterilization process is complete, the sterilized pans are removed from the sterilization unit and then most typically stored on shelves (not shown) until needed. Once needed, the sterilized pans are taken from storage, transported to the operating room and then unwrapped. The instruments are removed from the pan and laid out for use. If the sterilization filter medium 66 is breached in any manner before unwrapping, the contents are considered contaminated and therefore must be rewrapped and sterilized again before the contents can be used.

To reduce the risk of breaching the filter medium and contaminating the contents prior to use, the present invention provides a surgical instrument transport tray for holding, transporting and storing the wrapped instrument sterilization pans.

Referring to FIGS. 1 through 4, there is shown a surgical instrument transport tray 10 according to the present invention. The tray 10 includes a base member 12 and a plurality of sidewalls 14. The base member 12 has at least four sides and a top surface 16 and a bottom surface 18 separated by a thickness 20. The sidewalls 14 extend upwardly from the top surface 16 of the base member 12 adjacent the periphery 22 thereby forming a receiving chamber 24 for the wrapped sterilization pan 68 which nests within the receiving chamber 24 The sidewalls 14 terminate in a lip 26 removed from the top surface 16 of the base member 12. The lip 26 extends outwardly in a direction away from the receiving chamber 24 a distance at least one eighth the height of the sidewalls 14. By providing a lip of this size, it is more difficult for the contents of the trays 10 to bump into one another and possibly compromise the sterility of each of the units.

To permit handling of the tray 10, it can be provided with a handle rim 28 which depends downwardly from the lip 26 in spaced-apart relationship with the sidewalls 14 on at least two opposed side/edges of the base member 12. These handle rims 28 make a compact means of handling the tray 10 while supplying additional support and rigidity to the tray 10. To assist in proper balance of the tray when loaded, it is preferable that the rim's overall length be no greater than the overall length of the lip 26.

Ventilation to the underside of the wrapped sterilization pan 68 is provided through the use of a first plurality of spaced-apart holes 30 which extend completely through the thickness 20 of the base member 12 from the top surface 16 to the bottom surface 18. Generally this first plurality of holes 30 are between a half inch and an inch in diameter and occupy from about 15 to 25 percent of the total planar surface area of the base member 12.

It has been found that to maximize the structural rigidity of the tray 10, it is preferable to avoid using holes the size of the first plurality in the corners of the base member 12, i.e., the area adjacent the periphery 22 at the intersection of the sidewalls 14. As a result, the base member 14 can be provided with a second plurality of holes 32, which are smaller than the first plurality of holes 30, positioned adjacent the periphery 22 at the intersection of the sidewalls 14. As with the first plurality of holes, the second plurality of holes extend completely through the thickness 20 from the top surface 16 to the bottom surface 18. Preferably, these holes have a diameter less than three eighths of an inch.

Figure 1:
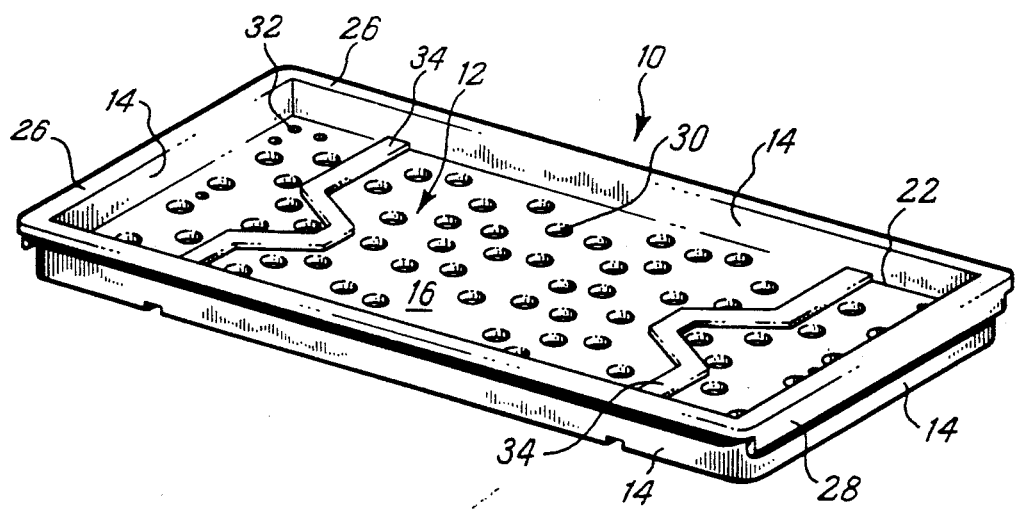
FIG. 1 is a perspective view of a surgical transport tray according to the present invention.
Figure 2:
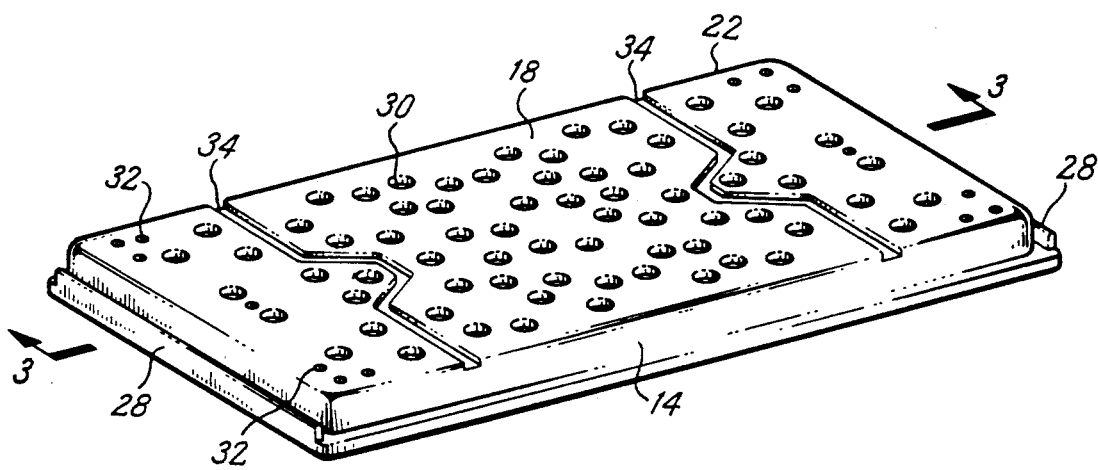
FIG. 2 is a perspective view of the bottom portion of a surgical transport tray according to the present invention.
Figure 3:
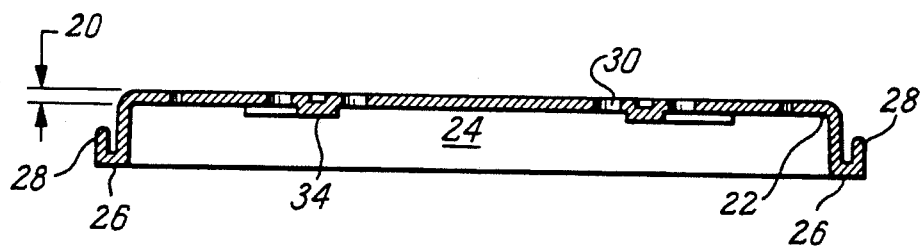
FIG. 3 is a cross-sectional side view of the surgical transport tray of FIG. 2 taken along line 3—3.

To further assist ventilation and prevent the sterilization filter medium 66 from being punctured or torn by objects projecting upwardly through the ventilation holes in the base member 12, the tray 10 may be provided with one or more support members 34 to lift and support the wrapped sterilization pan 68 above the top surface 16 of the base member 12. The support member 34 may be one or more ribs extending upwardly from the top surface 16 of the base member 12 and formed/molded integrally therewith as shown in FIGS. 1 through 3. Alternatively, the support member may be one or more individual projections extending upwardly from the base member 12 or outwardly from the sidewalls 14 (not shown). Preferably, the support members 34 extend upwardly no more than one-half the overall height of the sidewalls 14. In this manner the tray 10 does not become top-heavy when loaded with the wrapped sterilization pan 68.

Suitable materials for forming the surgical transport tray 10 of the present invention are primary moldable materials such as thermoplastic and thermoset resins including polypropylene, polysulfone and polycarbonate. It is also possible to use curable resins, as well as reinforced materials such as fiberglass-reinforced plastics and laminates using reinforcing layers of woven and nonwoven materials. The primary attributes are that the material chosen provides the requisite strength and durability while also being compatible with the sterilants and temperatures used during the sterilization, cleaning and decontamination processes.

Processes suitable for forming the trays of the present invention include injection molding as well as pressure/vacuum forming.

Having thus described the invention in detail, it should be appreciated that various other modifications and changes can be made without departing from the spirit and scope of the following claims.

What is claimed is:

1. A surgical instrument transport tray comprising:
a base member and sidewalls, said base member defining a periphery, a top surface and a bottom surface separated by a thickness and having at least four sides about said periphery of said base member, said sidewalls extending upwardly from said top surface of said base member adjacent said periphery to form a receiving chamber, said sidewalls terminating in a lip removed from said top surface and extending in a direction away from said receiving chamber, at least two of said sidewalls having a handle rim depending downwardly from said lip in spaced-apart relationship with said sidewalls, said base member defining a first plurality of holes extending completely through said thickness from said top surface to said bottom surface, said tray including a support member extending above said top surface of said base member a distance less than the overall height of said sidewalls, said tray further including an instrument sterilization pan nested within said receiving chamber, said pan being wrapped with a sterilization filter medium.

2. A surgical instrument transport tray comprising:

a base member and sidewalls, said base member defining a periphery, a top surface and a bottom surface separated by a thickness and having at least four sides about said periphery of said base member, said sidewalls extending upwardly from said top surface of said base member adjacent said periphery to form a receiving chamber, said sidewalls terminating in a lip removed from said top surface and extending outwardly in a direction away from said receiving chamber a distance at least one-eighth the height of said sidewalls, at least two of said sidewalls which are opposed to one another having a handle rim depending downwardly from said lip in spaced-apart relationship with said sidewalls, a support member extending above said top surface of said base member of said tray a distance less than the height of the sidewalls, said base member defining a first plurality of holes extending completely through said thickness from said top surface to said bottom surface, said base member defining a second plurality of holes extending completely through said thickness from said top surface to said bottom surface, said second plurality of holes being smaller than said first plurality of holes and positioned adjacent said periphery at the intersection of said sidewalls, said tray further including an instrument sterilization pan nested within said receiving chamber, said pan being wrapped with a sterilization filter medium.

* * * * *